United States Patent
Ring

(10) Patent No.: US 10,967,148 B2
(45) Date of Patent: Apr. 6, 2021

(54) PATIENT SPECIFIC GUIDE WIRE METHOD

(71) Applicant: Michael Ring, Spokane, WA (US)

(72) Inventor: Michael Ring, Spokane, WA (US)

( * ) Notice: Subject to any disclaimer, the term of this patent is extended or adjusted under 35 U.S.C. 154(b) by 540 days.

(21) Appl. No.: 15/885,818

(22) Filed: Feb. 1, 2018

(65) Prior Publication Data

US 2018/0154113 A1 Jun. 7, 2018

Related U.S. Application Data

(63) Continuation of application No. 15/005,520, filed on Jan. 25, 2016, now Pat. No. 9,919,130.

(51) Int. Cl.
*A61M 25/01* (2006.01)
*A61M 25/09* (2006.01)
*A61F 2/24* (2006.01)

(52) U.S. Cl.
CPC ........ *A61M 25/0113* (2013.01); *A61M 25/09* (2013.01); *A61M 25/09041* (2013.01); *A61F 2/2427* (2013.01); *A61F 2/2436* (2013.01); *A61M 2025/09116* (2013.01); *A61M 2025/09125* (2013.01)

(58) Field of Classification Search
CPC ...... A61F 2/243; A61F 2/2439; A61F 2/2427; A61F 2/2436; A61M 2025/09125; A61M 25/0113; A61M 2025/09116; A61M 25/09; A61M 25/09041; A61M 25/01; A61M 2025/09108; A61M 2025/09058; A61M 2025/09191
See application file for complete search history.

(56) References Cited

U.S. PATENT DOCUMENTS

| | | |
|---|---|---|
| 5,304,131 A | 4/1994 | Paskar |
| 6,752,800 B1 | 6/2004 | Winston et al. |
| 7,892,186 B2 | 2/2011 | Soukup et al. |
| 8,388,521 B2 | 3/2013 | Byers et al. |
| 8,992,480 B2 | 3/2015 | Gallacher et al. |
| 2010/0076408 A1* | 3/2010 | Krever .............. A61M 25/0147 604/529 |
| 2014/0012266 A1* | 1/2014 | Bonin, Jr. .............. A61B 17/15 606/88 |

* cited by examiner

*Primary Examiner* — Jason E Flick
(74) *Attorney, Agent, or Firm* — KNUBOX

(57) ABSTRACT

A guide wire control device and methods of use are described herein. A novel method for optimizing a guide wire for a patient is described. The method includes steps of scanning a patient's anatomy and then fabricating, or selecting, a guide wire with optimal geometry for a particular patient and/or procedure. The guide wire may optionally be secured to a guide wire control device for improved control during transcatheter surgical procedures.

19 Claims, 19 Drawing Sheets

PATIENT SPECIFIC GUIDE WIRE METHOD

CROSS REFERENCE TO RELATED APPLICATION

I hereby claim benefit under Title 35, United States Code, Section 120 of U.S. patent application Ser. No. 15/005,520 filed Jan. 25, 2016 entitled "Catheter Guide Wire Control Device". This application is a continuation of the Ser. No. 15/005,520 application. The Ser. No. 15/005,520 application is currently pending. The Ser. No. 15/005,520 application is hereby incorporated by reference into this application.

STATEMENT REGARDING FEDERALLY SPONSORED R&D

Not related to this application.

TECHNICAL FIELD

This invention relates to guide wire control devices, and more particularly to guide wire control devices for use in procedures involving catheter deployed medical devices.

BACKGROUND OF THE INVENTION

Guide wires are commonly used in the field of medicine. They are used to navigate the torturous pathways of anatomy. Guide wires, also called stylets, can be inserted through an orifice of a body, or surgically inserted. The wire is pushed, turned, and flexed at a proximal end which remains outside the body. The forces applied to the proximal end translate down the wire to a distal end. The distal end can provide various procedure specific functions inside the body. A guide wire can be made from various materials, with metal being common. Guide wires also come in a wide range of diameters, typically being 0.050 inches or less. Guide wire coatings and finishes can provide benefits for a given procedure. A common application for a guide wire is with endovascular procedures.

The practice of repairing an artery through the use of a stent is well known in the field of medicine. In general and as an example of a typical guide wire application, a guide wire is inserted into an artery using the Seldinger technique. The femoral artery, near the groin, is a common entry point. The guide wire is advanced to a desired location. A delivery catheter with a stent attached is placed around the guide wire through a central lumen and is advanced along the length of the guide wire. Depending on the type of stent, the stent may be deployed by expansion of a balloon or in the case of nitinol stents, by withdrawing a sheath covering the nitinol stent and allowing the nitinol stent to assume its memory shape through self-expansion. A well known issue with self-expanding nitinol stents is their tendency to "jump" as the sheath on the delivery catheter is retracted, which limits the precision of the stent deployment and can result in malposition of the stent. Once the stent is deployed, the delivery catheter is removed from the body.

A recent advancement in the treatment of cardiac disease is transcatheter devices to either replace or repair dysfunctional native cardiac valves. These include the aortic, mitral, tricuspid and pulmonary valves. Rather than using an open heart procedure to replace or repair a defective valve in a patient's heart, a minimally invasive catheter system is used to deploy an expanding structure containing a replacement valve material. The new prosthetic valve displaces the leaflets of the defective valve and takes over the function of regulating blood flow through the heart and artery. Transcatheter prosthetic valve technology is dominated by two technologies. The first uses a stainless steel (or other metal composition) stent that is expanded by an inflatable balloon. The second utilizes a nitinol metallic mesh that is cooled and compacted, and then expands to a desired shape when the metal approaches body temperature.

Transcatheter valve replacement presents marked challenges over other endovascular procedures that utilize a catheter. Unlike typical endovascular procedures which occur in constrained tubular blood vessels where there is limited spatial movement of the devices, transcatheter valve procedures by their nature are performed in the heart with relatively large and spatially complicated chambers that pose significant challenges to guidewire management and device manipulation by the surgeon. First, the prosthetic valve must be located extremely precisely relative to the natural valve prior to the prosthetic valve being expanded in place. The replacement valve needs to be located plus or minus 1-3 mm in depth relative to its target location. The surgeon may use fluoroscopic imaging to determine optimal depth of the valve prior to deployment. From the proximal end, the surgeon manipulates the guide wire and catheter sheath to achieve the desired deployment location of the prosthetic valve. An improperly deployed valve can lead to perivalvular regurgitation or catastrophic embolization of the device into either the heart or aorta. Second, in order to minimize canting of the prosthetic valve, the deployed valve should be positioned ideally in the center of the diseased native valve. Again, the surgeon uses forces on the proximal end of the guide wire and catheter to attempt to manipulate the location of the valve relative to the walls of the defective valve. Third, during the procedure the surgeon in addition to maintaining optimal forces on both the catheter sheath and guide wire, has additional responsibilities of managing the operating room, and scanning fluoroscopic, echocardiology and hemodynamic monitors. When the replacement valve is optimally located, the surgeon must maintain optimal pressure on both the guide wire and the catheter to resist translational forces created by the expanding valve. Wherein many endovascular procedures utilize the guide wire only for navigation purposes, in new advanced procedures such as transcatheter aortic valve replacement, the guide wire is often the key element throughout the procedure and requires constant attention. The transcatheter aortic valve replacement guide wire provides navigation of the catheter sheath as well as impacting location of the deployed valve. With guide wires being small in diameter, often coated in low friction materials, and with bodily fluids present, maintaining optimal pressure on the guide wire throughout the valve replacement procedure can be challenging and fatiguing for the surgeon. Although the field of transcatheter mitral valve replacement and repair is less mature than transcatheter aortic valve replacement, the challenges of accurate device deployment may be even greater due to the factors outlined above.

In these respects, the present invention departs from conventional concepts of the prior art by providing a guide wire control device for use in catheter based medical procedures. The present invention also provides an improved way to achieve optimal valve deployment in trancatheter valve replacement and repair procedures.

SUMMARY OF THE INVENTION

The present invention takes a very different approach to controlling a guide wire during medical procedures in comparison to the prior art.

The present invention provides a device for controlling a guide wire during a surgical procedure. A guide wire is retained by a lock mechanism to a translational assembly. The translational assembly moves relative to a stationary assembly. The movement of the translational assembly, and resulting guide wire, is controlled by the interaction of a spring device that engages with an array of features in the stationary assembly. The angle of engagement of the spring device to the stationary assembly can be changed to provide optimal translational resolution and overall movement. The stationary assembly may be attached to a catheter delivery device or the two can be integrated.

Control of a guide wire, according to the present invention, provides the advantages of reducing fatigue of the surgeon and better locational accuracy of catheter delivered medical devices. The preferred embodiments for both the apparatus and process is described for use in heart valve repair and replacements, but the present invention is applicable to any medical procedure utilizing a catheter.

Also described in the present invention are improved guide wire shapes that are optimized for procedures that utilize a guide wire for not only navigating tortuous lumens, but for also providing structure for use within open cavities such as the heart. The present invention provides guide wire distal end shapes and a process for customizing a guide wire for use with a particular patient's heart. Although described for use in heart valve replacement and repairs as part of the best mode of the present invention, optimizing guide wires as described herein is applicable to any guide wire based medical procedure.

These and other features, aspects, and advantages of the present invention will become better understood with regard to the following description, appended claims, and accompanying drawings.

BRIEF DESCRIPTION OF THE DRAWINGS

Preferred embodiments of the invention are described below with the reference to the following accompanying drawings:

FIG. 15 is a section view of the translating assembly inserted into the stationary assembly. The view is sectioned through the middle of the wire control device. Also shown is detail area 15a.

DETAILED DESCRIPTION OF THE PREFERRED EMBODIMENTS

Many of the fastening, connection, wiring, control, manufacturing and other means and components utilized in this invention are widely known and used in the field of the invention, and their exact nature or type is not necessary for a person of ordinary skill in the art or science to understand the invention; therefore they will not be discussed in detail. Furthermore, the various components shown or described herein for any specific application of this invention can be varied or altered and anticipated by this invention and the practice of a specific application or embodiment of any element may already be widely known or used in the art, or persons skilled in the art or science; therefore, each will not be discussed in significant detail.

The present invention, as described, is used to control guide wires during medical procedures. Guide wires can be used to navigate tortuous pathways, can be used in advance of a delivery catheter, or used in conjunction with a delivery catheter to perform a desired medical procedure. Although the present invention is primarily described for use within an aortic artery, it should be appreciated that the present invention should not be construed to be limited to any particular body lumen. Other applicable lumens include, but are not limited to, gastrointestinal and urine lumens. Similarly, the present invention is primarily described for use with heart valve replacement procedures, but the present invention should not be construed to be limited to any particular procedure. Other applicable procedures include, but are not limited to, coronary angioplasty, stenting procedures and angiograms.

Figure 1:
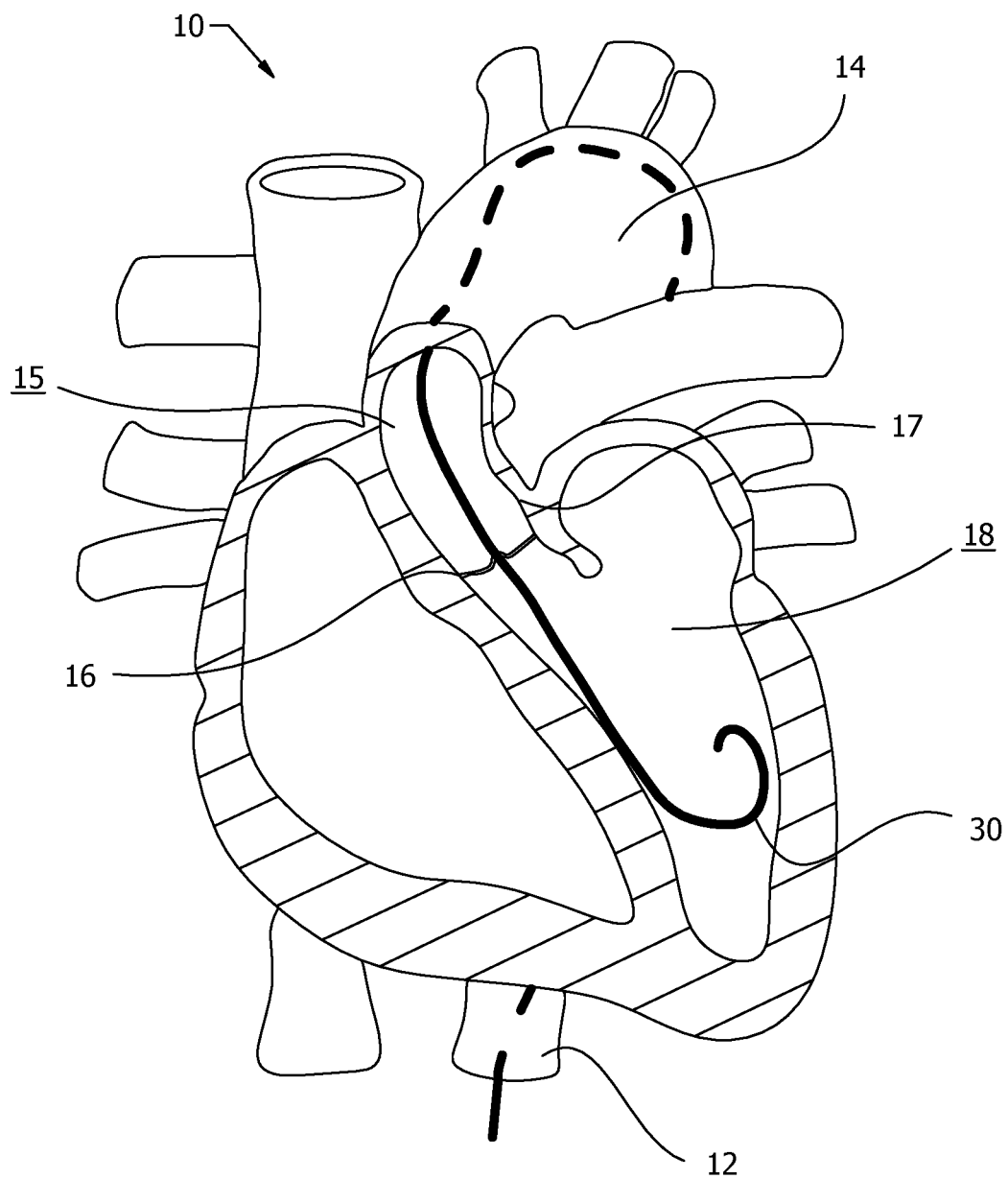
FIG. 1 is a front partial section view of a heart with a guide wire inserted through the aortic artery and into the left ventricle of the heart.
Figure 2:
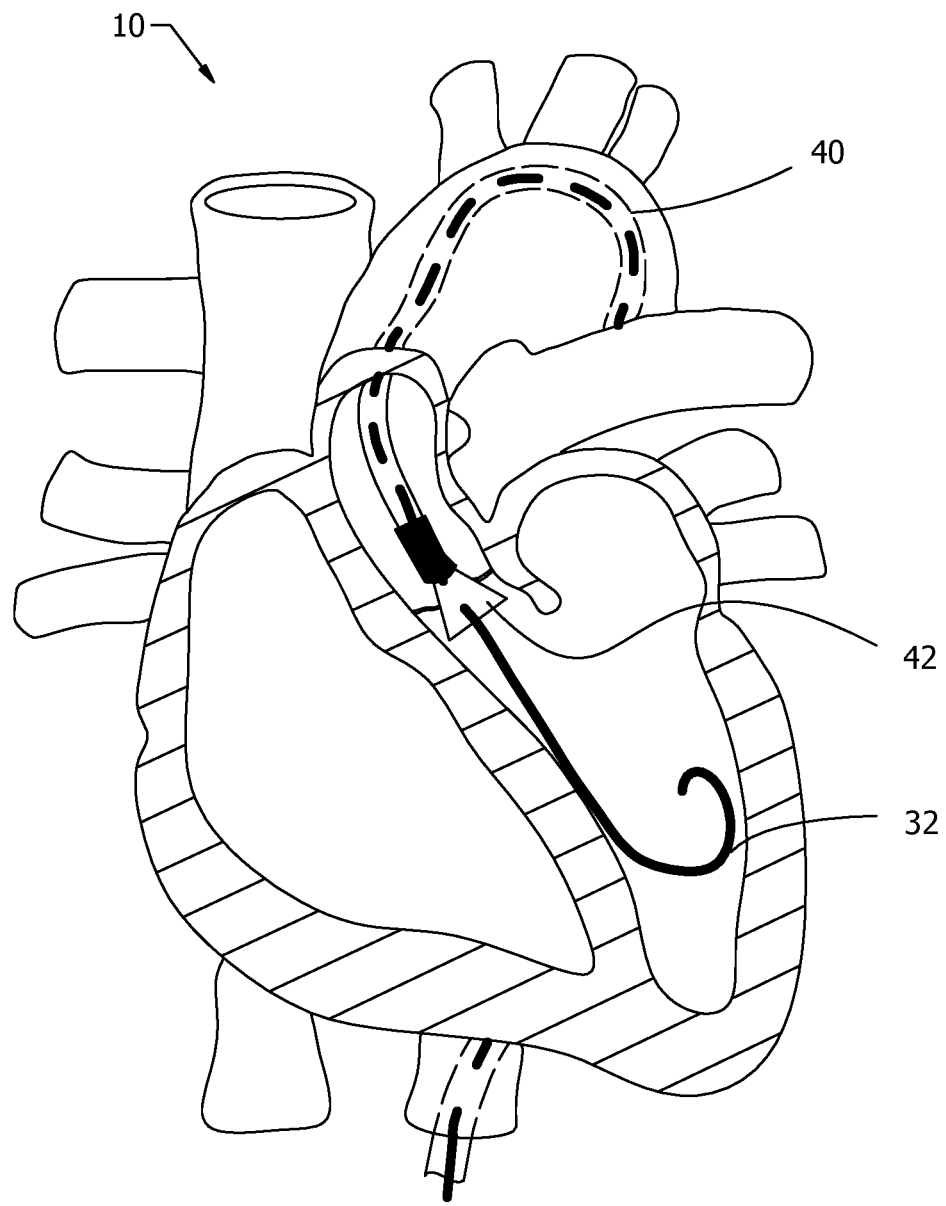
FIG. 2 is the same front partial view as FIG. 1, but with a catheter sheath and artificial valve inserted around the guide wire of FIG. 1 and into the heart.
Figure 3:
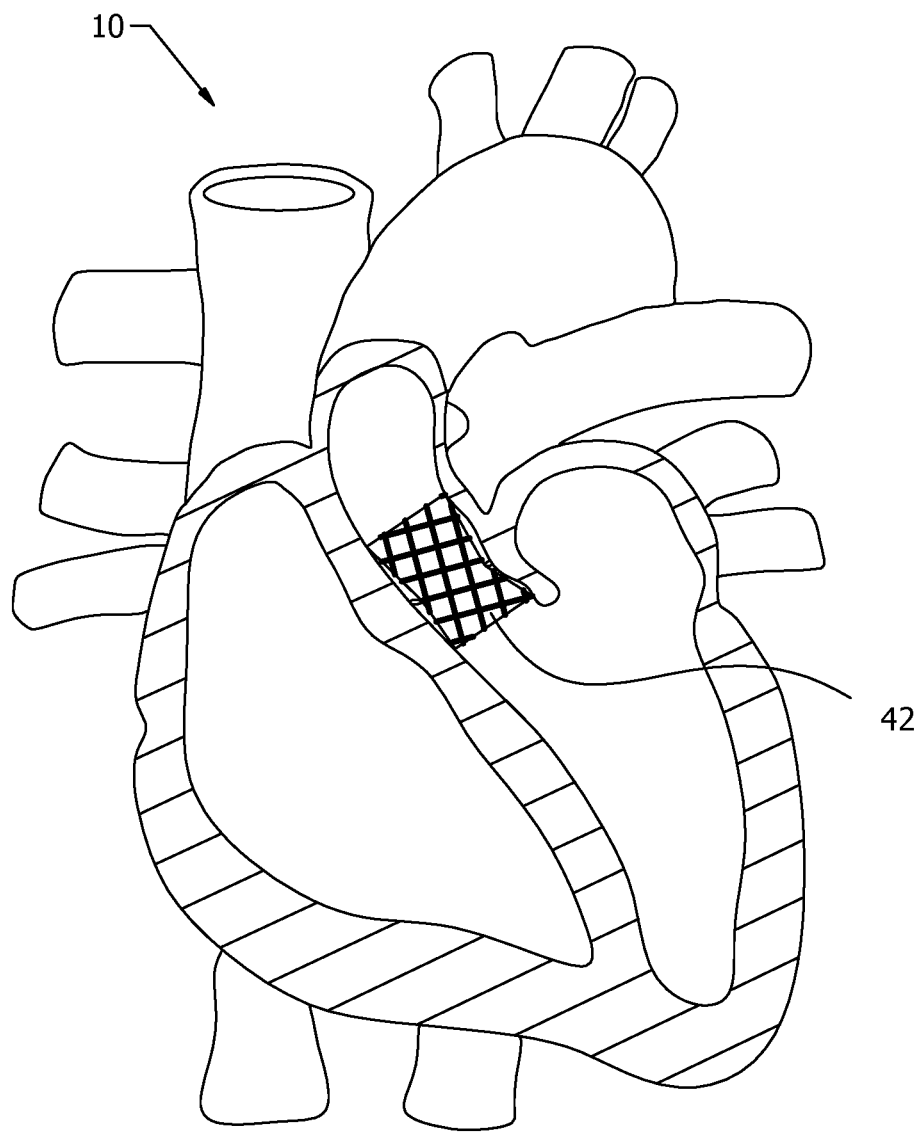
FIG. 3 is the same front partial section view of FIG. 1 and showing a deployed artificial valve.

Now referring to the figures, FIGS. 1, 2 and 3 show a partial section view of a heart 10. The anatomy of heart 10 is well known in the art of medicine and a detailed understanding is not necessary for one to understand and appreciate the present invention; therefore it will not be described in significant detail. Components of heart 10 shown in the accompanying drawings are in the non-limiting context of using the present invention in an aortic valve replacement procedure.

In replacing an aortic valve and referring to FIG. 1, a guide wire 30 is advanced through an aortic artery 12, through a natural aortic valve 16, and into a left ventricle 18. Aortic artery 12 starts in the abdomen. An aortic arch section 14 comes from the back side of the heart and bends towards an ascending aorta section 15 which is just before aortic valve 16. Blood leaving left ventricle 18 escapes through natural aortic valve 16. Aortic valve 16 is surrounded by an aortic valve annulus section 17. It should be appreciated that the lumens of heart 10 are complex in shape and trajectory.

Figure 4:
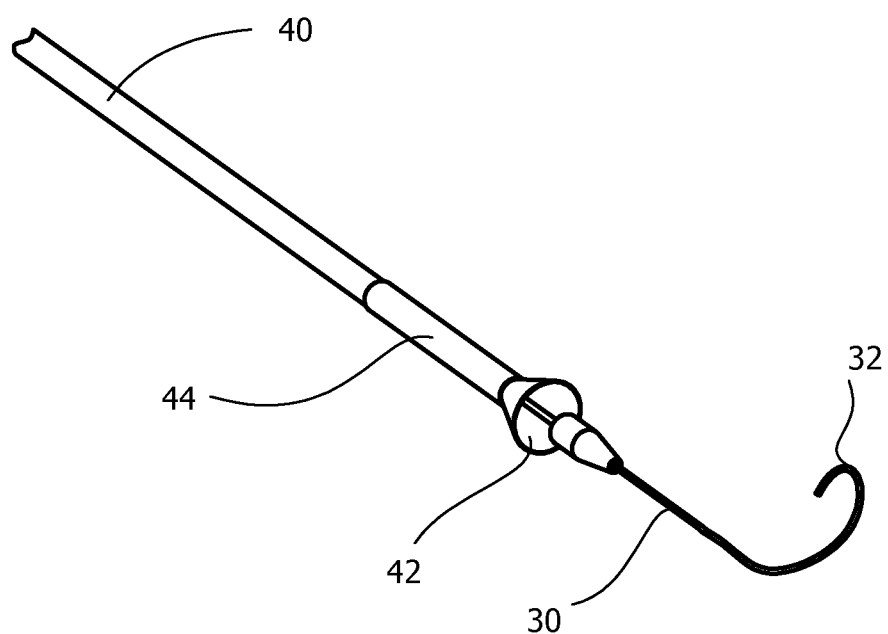
FIG. 4 is a perspective view showing a distal end of a prior art heart valve deployment device.

FIG. 4 shows the distal end of a prior art heart valve replacement delivery system. Although the present invention is not limited to any particular delivery system, one such system is commercially produced by MEDTRONIC® under the tradename COREVALVE®. Guide wire 30 has a guide wire distal end 32 which is shown manufactured with a curl. Guide wire 30 is approximately 0.035 inches in diameter and made from a metallic material which is coated in a low friction material, such as polytetrafluoroethylene. Guide wire distal end 32 is more flexible than the rest of guide wire 30 which allows it to more easily navigate tortuous pathways with minimal damage to adjacent tissue. A catheter sheath 40 is advanced over guide wire 30. Catheter sheath 40 is connected to a capsule 44 which houses a prosthetic valve 42. In FIG. 4, prosthetic valve 42 is shown in a partially deployed state. With advancement of catheter sheath 40, prosthetic valve 42 is completely encapsulated within capsule 44. With retraction of catheter sheath 40, prosthetic valve 42 is deployed.

The application of the prior art heart valve delivery system of FIG. 4 is shown in FIGS. 1, 2 and 3. In FIG. 1, guide wire 30 has been advanced through aorta 12, has navigated both aortic arch 14 and ascending aorta 15 sections, has penetrated though natural valve 16, and has guide wire distal end 32 located within left ventricle 18. The curve of distal end 32 is shown against a wall of left ventricle 18 which can provide some force against guide wire 30. It should be appreciated at the stage of FIG. 1, the surgeon has advanced guide wire 30 by applying forces to the proximal end of guide wire 30. Imaging and feel ensures guide wire 30 is properly placed in heart 10. Guide wire 30, when placed in heart 10, has some impact to the normal function of heart 10. Therefore, it is desirable for the surgeon to act quickly and precisely to deploy prosthetic valve 42.

FIG. 2 shows catheter sheath 40 advanced over and along guide wire 30. Because guide wire 30 is used in conjunction with catheter sheath 40 to locate prosthetic valve 42 in its optimal location, it should be appreciated that the surgeon may have to move guide wire 30 in relationship to catheter sheath 40. Optimal location of prosthetic valve 42 in relationship to natural valve 16 and aortic annulus section 17 may be plus or minus one to three millimeters. Once optimal location of prosthetic valve 42 has been achieved both radially and in depth, the surgeon retracts catheter sheath 40 causing deployment of prosthetic valve 42. The angled expansion of prosthetic valve 42 can cause a "jump" translation of either catheter sheath 40, guide wire 30, or both, during deployment. Translations during deployment can negatively impact deployment of prosthetic valve 42. To maintain a successful deployment of prosthetic valve 42, the surgeon must maintain optimal locations and forces of both catheter sheath 40 and guide wire 30. FIG. 3 shows prosthetic valve 42 deployed.

Figure 5:
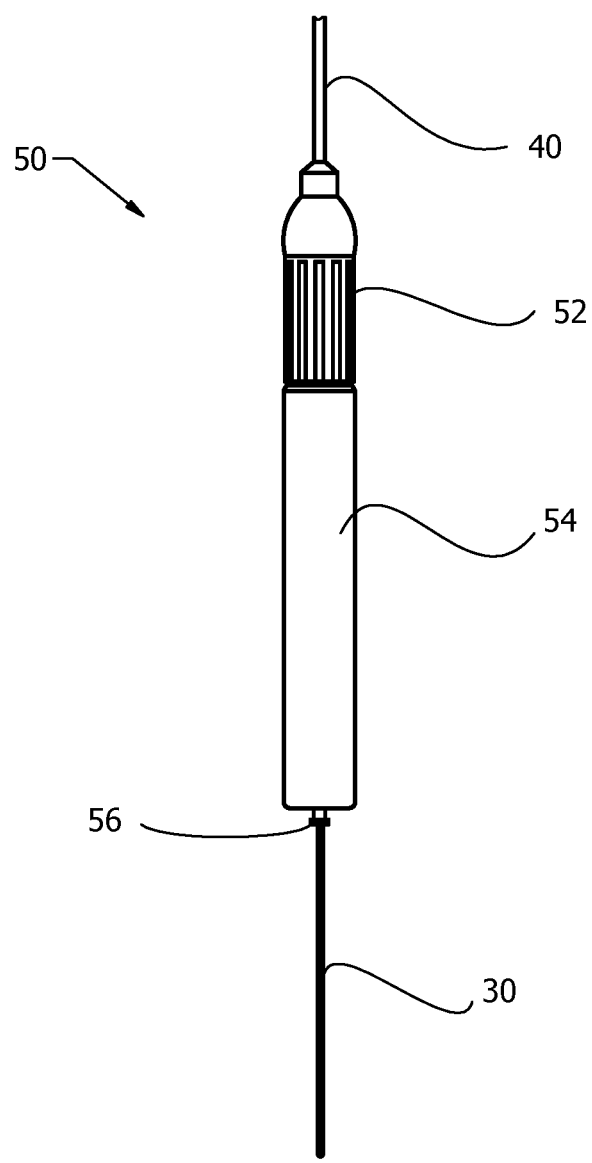
FIG. 5 is a top view of a proximal end of a prior art heart valve deployment device.

FIG. 5 shows a prior art heart valve deployment device 50 which controls the advancement of sheath 40 and deployment of prosthetic valve 42. The surgeon holds heart valve deployment device 50 via deployment device handle 54. Prosthetic valve 42 is deployed by turning a deployment actuator 52 relative to deployment device handle 54. Guide wire 30 translates through deployment device 50 and exits through a Luer fitting 56. During a prior art procedure, the surgeon must maintain optimal forces on guide wire 30 and manage its location with respect to deployment device 50. Managing guide wire 30 relative to deployment device 50 is done with whatever available or remaining fingers the surgeon has during the procedure.

Figure 6:
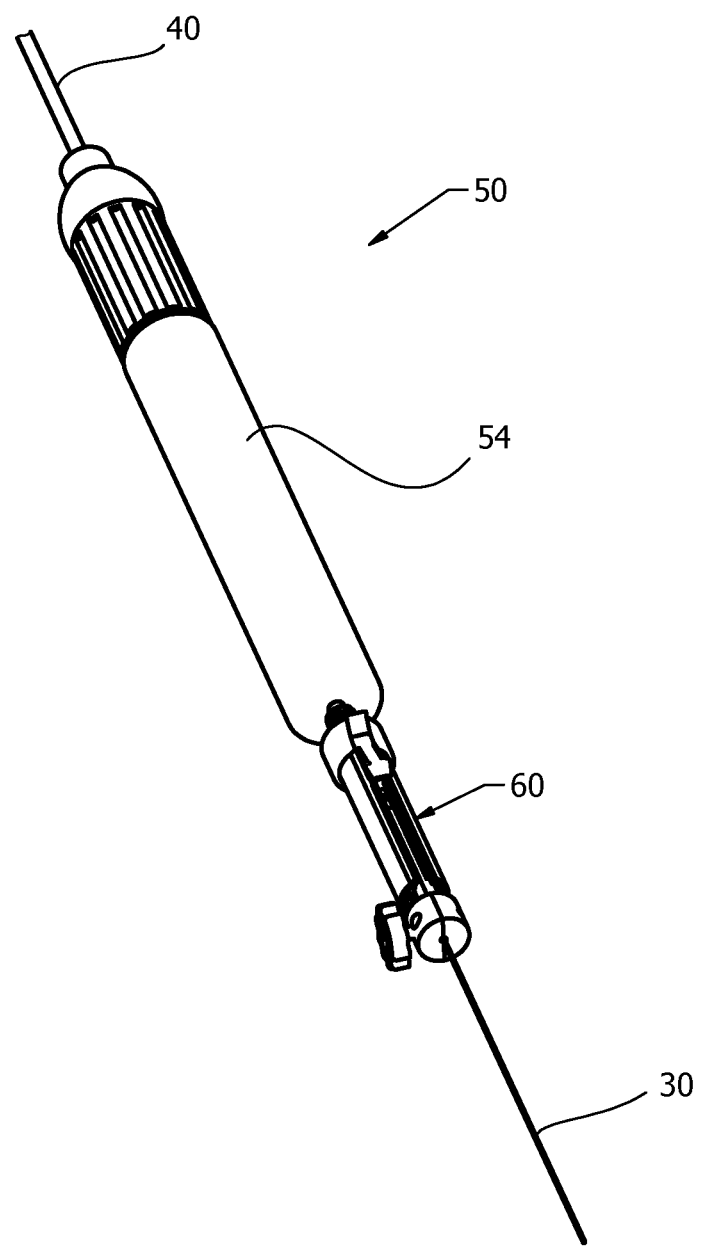
FIG. 6 is a perspective view of a guide wire control device, according to the present invention. The guide wire control device is attached to the end of the heart valve deployment device of FIG. 5.

FIG. 6 shows a guide wire controller 60 according to the present invention. Guide wire controller 60 is shown attached to deployment device 50. Guide wire controller 60 is used to achieve and maintain optimal position of guide wire 30 in heart 10 and with respect to catheter sheath 40. Guide wire controller 60 provides the means of maintaining a position of guide wire 30 in the tortuous pathways of a body.

Figure 7:
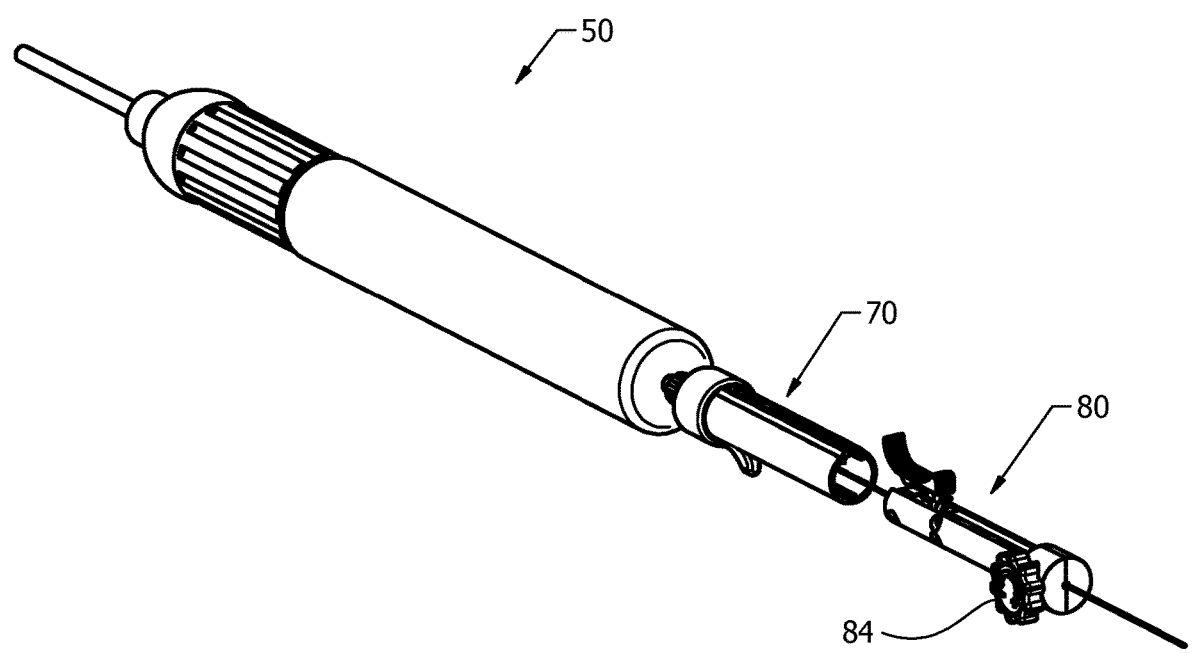
FIG. 7 is a perspective view of the guide wire control device of FIG. 6 and showing a stationary assembly separated from a translating assembly.
Figure 8:
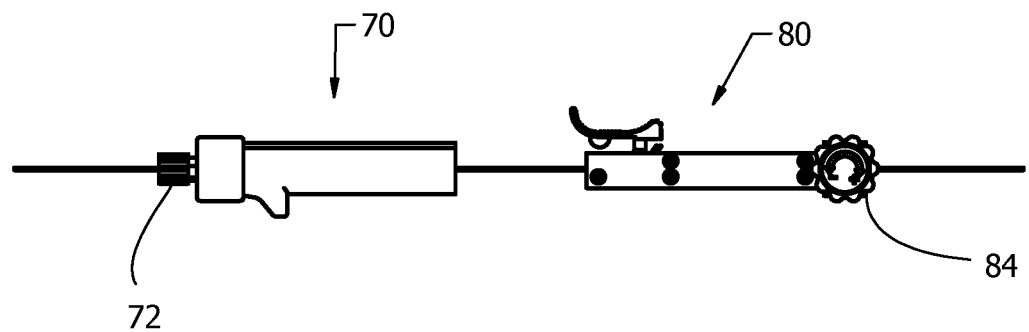
FIG. 8 is a side view of the guide wire control device of FIG. 7 and showing the stationary assembly detached from the translating assembly.

As shown in FIG. 7, guide wire controller 60 is comprised of a stationary assembly 70 and a translational assembly 80. Stationary assembly 70 is removably attached to deployment device 50 by connecting a corresponding Luer connector 72 to Luer fitting 56 of deployment device 50. Translational assembly 80 attaches to guide wire 30 by means of guide wire lock 84. Translational assembly 80 is inserted into stationary assembly 70 and the relative movement between them controlled. The result is that translational assembly 80 controls the translation of guide wire 30 relative to deployment device 50.

Stationary Assembly

Figure 10:
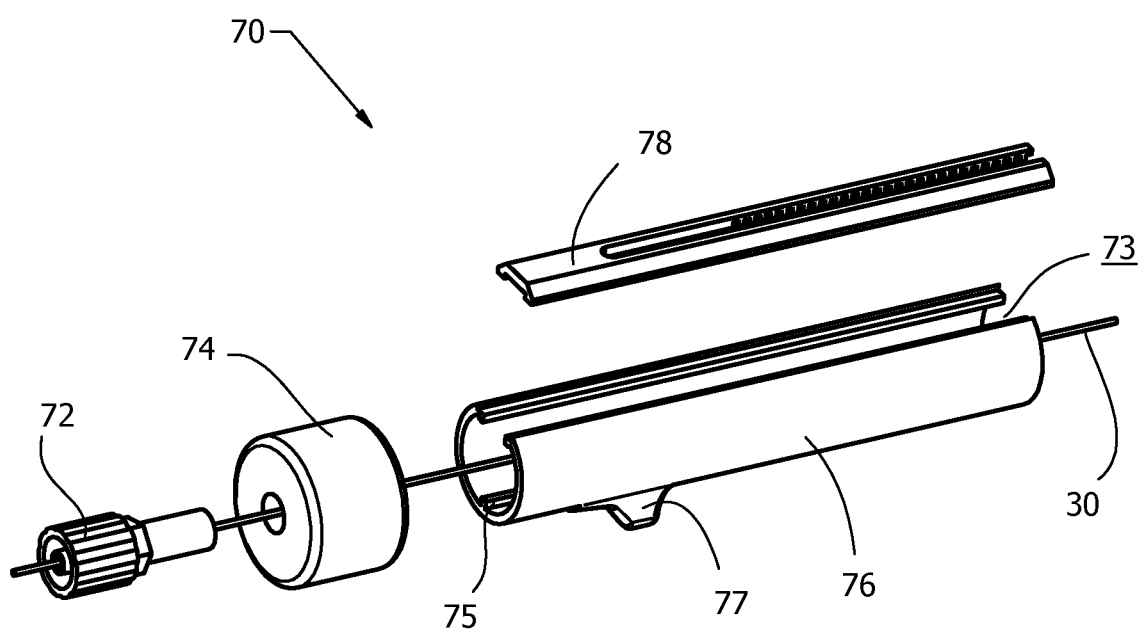
FIG. 10 is a front perspective and exploded view of the stationary assembly of the present invention.

Stationary assembly 70 is best seen in the exploded view of FIG. 10. A main tube 76 provides the primary structure of housing translational assembly 80. Main tube 76 is open on both of its ends and contains features for engaging with translational assembly 80. Translational assembly 80 is able to translate axially through main tube 76 but is not able to rotate with respect to main tube 76. Although the present invention should not be limited to any particular dimension or shape of any particular component, it has been found and according to the best mode of the present invention, main tube 76 is approximately 4 inches in length and has an outside diameter of 0.75 inches. ABS type plastic, with a wall thickness of 0.06 inches has been found to be acceptably rigid, but other materials and wall thickness may be used within the sprit and scope of the present invention. For example, metallic materials may be acceptable for use. Preferably, main tube 76 includes finger support 77 which aids the user in using guide wire control device 60.

Figure 11:
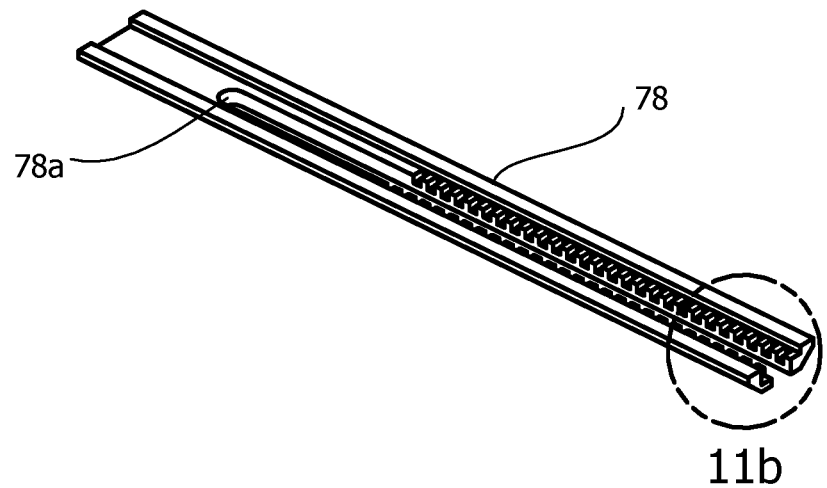
FIG. 11 is a bottom perspective view of the groove member of the stationary assembly and showing detail area 11b.
Figure 11B:
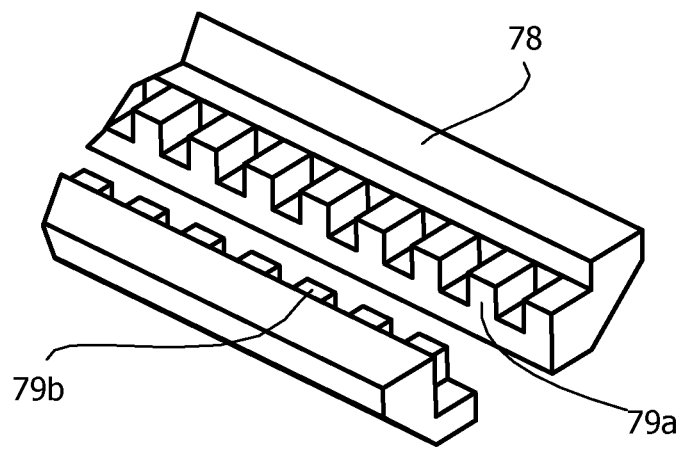
FIG. 11B is a detailed perspective view of the groove member of FIG. 11.
Figure 12:
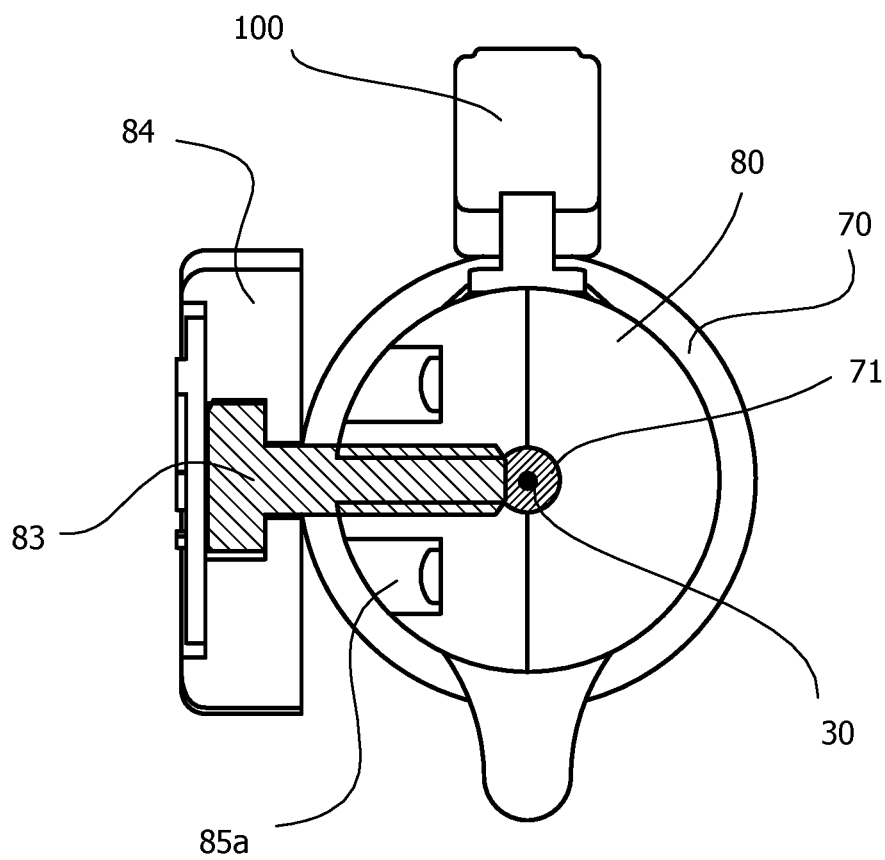
FIG. 12 is a section view of the guide wire control device in the direction of section arrow C of FIG. 9.

As shown in FIG. 10, the top of main tube 76 contains an open channel 73 which is approximately 0.25 inches wide. Open channel 73 is used to bond a groove cap 78. As best shown in FIGS. 11 and 12, the underside of groove cap 78 contains a first array of grooves 79a and a second set of grooves 79b. Groove arrays 79a and 79b are used to engage with a spring 110 of translational assembly 80 which will be later described in further detail. Groove arrays 79a and 79b are cavities that preferably extend partially through the thickness of groove cap 78. Although cubic sections are shown, it should be appreciated that any shape of cavity can be used within the present invention. The spacing of groove arrays 79a and 79b correspond with the desired movement accuracy of translational assembly 80 and resulting guide wire 30 relative to main tube 76. According to the best mode of the present invention wherein desired translational accuracy of guide wire 30 and prosthetic valve 42 is single millimeters or less, grooves 79a is shown staggered to groove 79b. With limitations in both strength and manufacturability of groove cap 78, staggering grooves 79a and 79b provides the means for creating translational accuracy greater than a single array of grooves or multiple sets of aligned grooves. Manufacturing strong alternating walls having less than one millimeter in width can be at best challenging. Although staggered grooves is primarily described herein as part of the best mode of the present invention, it should be appreciated that a single set of grooves may be acceptable for a given procedure or device, all within the spirit and scope of the present invention. Groove cap 78 has a central channel 78a which extends substantially the length of groove 78. Central channel 78a contributes to the guide structure for translational assembly 80.

Bonded to the front of main tube 76 is tube ring 74. Tube ring 74 provides both manufacturing flexibility to main tube 76 and provides additional strength to main tube 76. On the forward surface of tube ring 74 is Luer connector 72. Luer fittings are common in the art of medical devices and Luer connector 72 may be any type of common fitting ranging from threaded, fastened with a nut behind tube ring 74, or can be either male or female. Many standard Luer fittings are commercially available from the Nordon® Corporation.

Combined, stationary assembly 70 is able to be removably attached to deployment device 50, provides controlled axial movement of translational assembly 80, and rotational constrains translational assembly 80. Although the components of stationary assembly 70 are shown as separate attachable elements that help optimize manufacturing, it should be appreciated that stationary assembly 70 may be a single structure. For instance, a 3D printed version of stationary assembly 70 may include groove cap 78, tube ring 74, and other features that are created together. The present invention should not be construed to be limited to separate and attachable components.

Translational Assembly

Translational assembly 80 provides controlled movement of guide wire 30 relative to stationary assembly 70. Translational assembly 80 has a first sliding member 86a and a second sliding member 86b. First sliding member 86a is a near mirror image of second sliding member 86b with the exceptions of a plurality of fastener recess pockets 85a in second sliding member 86a and a plurality of fastener holes 85b in the back of sliding member 86a. Screw fasteners are retained by threads in fastener holes 85b. Fastener recess pockets 85a are sized to ensure that the fastener heads do not extend beyond the outside surface of first sliding member 86a. A stop edge 89 is formed by mating first and second sliding member 86a and 86b. Stop edge 89 is used to make contact with the back edge of stationary assembly 70 and to limit the travel of guide wire 30 relative to stationary assembly 70. Through the center of both first and second sliding member 86a and 86b is a central channel 81 which is sized larger than guide wire 30. Central channel 81 allows for guide wire 30 to be easily inserted through guide wire controller 60.

Sandwiched between first and second sliding members 86a and 86b are components which both capture guide wire 30 and provide controlled movement between stationary assembly 70 and translational assembly 80. These components are best seen in FIGS. 9, 13, 14 and 15.

Figure 13:
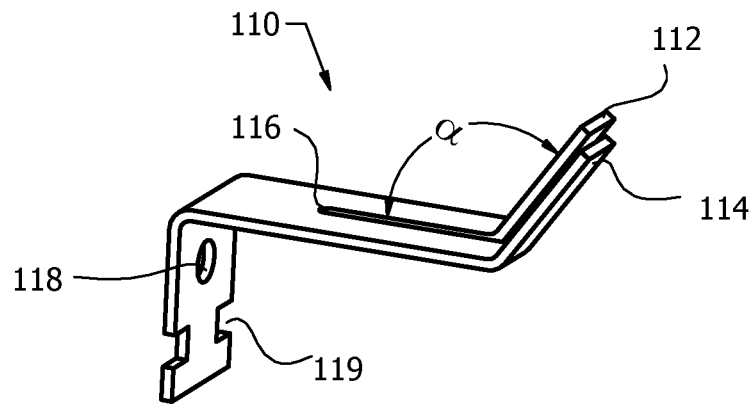
FIG. 13 is a rear perspective view of a spring according to the present invention.

A spring 110 is captured by the assembled sliding members 86a and 86b. A spring retaining slot 119 matches a corresponding protrusion in sliding members 86a and 86b. Retaining slot 119 ensures that spring 110 cannot move up or down when assembled. To remove the complexity of manufacturing a slot the thickness of spring 110 (0.010 to 0.020 inches), a removable spring holdback block 120 is placed on the back side of spring 110. The result is that spring 110 is captured and fixed by assembled sliding members 86a and 86b. With spring 110 extending across central channel 81, a spring opening 118 allows guide wire 30 to pass through spring 110. Spring 110 has a first spring tine 112 and a second spring tine 114. A tine slot 116 enables first spring tine 112 to move independently of second tine 114. Spring tines 112 and 114 are bent at an angle of "a" to the main section of spring 110. Spring tines 112 and 114 may be formed offset to each other as shown in FIG. 13, or alternatively can be formed in the same plane. The reasons for offsetting are discussed later in the assembly section. Although the present invention should not be construed to be limited to any particular size or shape of spring, according to the best mode, spring 110 is 0.015 inches thick, 0.25 inches wide and made from heat treated spring steel.

Figure 14:
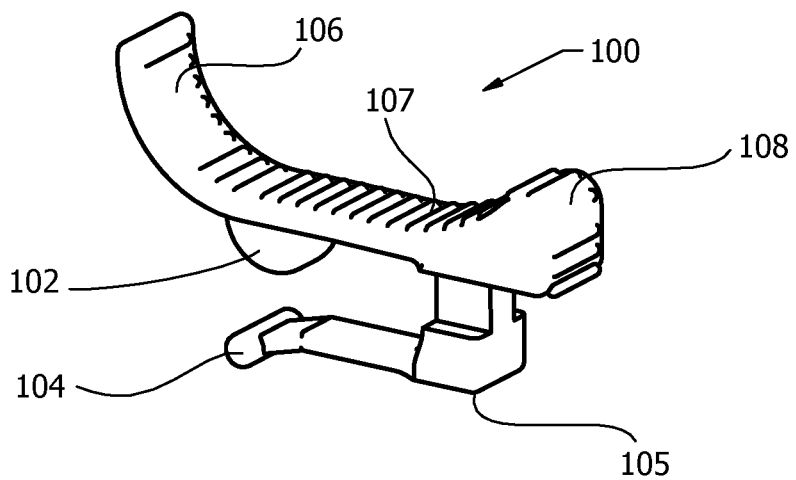
FIG. 14 is a rear perspective view of an actuator that fits within the stationary assembly.
Figure 15:
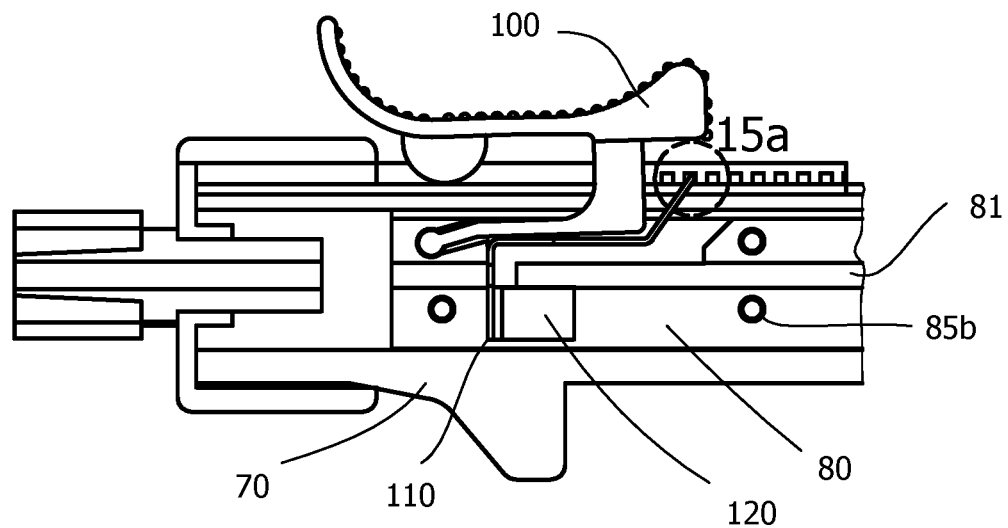

An actuator 100 is best shown in FIG. 14 and FIG. 15. Actuator 14 has a pin 104 that is captured by a corresponding cavity in sliding members 86a and 86b. Actuator 100 acts as a lever that makes contact with spring 110 at actuator contact surface 105. The distance between actuator pin 104 and actuator contact surface 105 relative to the users thumb determines how much force is applied by actuator spring contact surface 105 onto the first and second spring tines 112 and 114. At the top of actuator 100 is where a user engages their thumb or finger for controlled movement of translational assembly 80. A push surface 106 at the front of actuator 100 allows the surgeon to move translational assembly 80 forward and extend guide wire 30. Push surface 106 is curved upward to partially capture the users thumb in the event that fluids have made actuator 100 slippery. When applying a force on push surface 106, contact surface 105 does not push down spring tines 112 or 114. Below push surface 106 is actuator guide 102. The width of actuator guide 102 is just slightly narrower than the width of central channel 78a of groove cap 78. Actuator guide 102 facilitates proper alignment of actuator 100 relative to main tube 76. Generally above spring contact surface 105 is a release surface 107. When a user pushes down on release surface 107, contact surface 105 applies a downward force on spring tines 112 and 114. Behind release surface 107 is a combination surface 108. When a user applies a force to surface 108, a slight change in the angle of force can cause contact surface 105 to apply a lateral force to translational assembly 80, a vertical force onto spring tines 112 and 114, or both a lateral and vertical force.

At the back end of translational assembly 80 is a lock 84. As shown in the cross section of FIG. 12, lock 84 contains and captures a hex headed screw 83. Screw 83 engages with threads of first sliding member 86a which allows screw 83 to move radially towards guide wire 30. Captive to first and sliding members 86a and 86b is a friction sleeve 71. Friction sleeve 71 is preferably a cylinder made from a high friction compliant polymer that both protects guide wire 30 form deformation from screw 83 and creates a high friction surface against it. Friction sleeve 71 preferably has a length long enough to cover the diameter of screw 83 and a central hole capable of passing guide wire 30 when in the relaxed state. With a PTFE coated guide wire material having a very low coefficient of friction, there is a need for approximately 100 pounds of radial force needed to secure guide wire 30 to translational assembly 80. Utilizing a fine pitch, such as but not limited to 32 threads per inch, has been found to provide acceptable grip on guide wire 30 while requiring an acceptable turning force on lock 84.

Figure 15A:
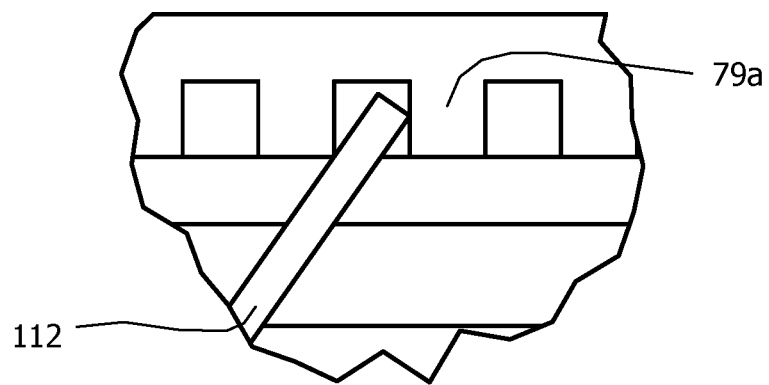
FIG. 15a is a detailed view of FIG. 15 and showing the interaction of a tine of the spring engaged with the groove member of FIG. 11.

The interaction of translational assembly 80 with stationary assembly 70 is best shown in FIGS. 15 and 15a. First spring tine 112 is shown engaged with first array of grooves 79a. The angle "a" of spring 110 enables first spring tine 112 to deflect downward when translational assembly 80 moves forward, without any downward force from actuator 100. During forward movement, first spring tine 112 moves up and down from groove to groove of first groove array 79a. In a similar fashion, second spring tine 114 engages with second array of grooves 79b. By staggering engagement of first spring tine 112 to first array of grooves 79a and second spring tine 114 to second array of grooves 79b, either first or second spring tine 112 and 114 is always engaged in a groove. Although forward movement of translational assembly 80 with respect to stationary assembly 70 causes spring tines 112 and 114 to flexibly engage, backward movement is resisted. A backward force on translational assembly 80 is transferred up through spring 110 and either tine 112 or 114 pushes against a groove in groove array 79a or 79b. With groove arrays 79a and 79b only partially extending through groove cap 78, spring tines 112 and 114 are vertically captured and can take substantial forces. A downward force on actuator 100 causes actuator surface 105 to push down spring tines 112 and 114 and disengage them from groove arrays 79a and 79b.

Use

There are several scenarios for use of the present invention. As one general example, the proximal end of guide wire 30 is inserted through Luer connector 72 of stationary assembly 70. In this scenario, translational assembly 80 is already inserted into stationary assembly 70. Guide wire 30 is pushed through translational assembly 80 with lock 84 in a screwed outward position. Translational assembly 80 is preferably in the back position of stationary assembly 70 with either tine 112 or 114 engaged in the first grove of either groove array 79a or 79b. The user then optionally attaches stationary assembly 70 to deployment device 50 by securing Luer connector 72. With guide wire 30 loose, the user can push or pull guide wire 30 through guide wire controller 60. When guide wire 30 is close to the desired location within a lumen of the body, turning lock 84 applies a grip pressure on guide wire 30 causing it to move with translational assembly 80. The user than advances translating assembly 80 forward by applying a force to either push surface 106 or combination surface 108. The forward force applied to actuator 100 causes spring tines 112 or 114 to deflect down due to angle "a". Angle "a" disengages spring tines 112 or 114 with forward motion in increments of the combined pitch of groove arrays 79a and 79b. The repeated engagement of spring tines 112 and 114 provide both tactile and audible feedback with the movement of translational assembly 80. When a desired location is achieved, the user can remove pressure on actuator 100 and guide wire 30 stays in the desired location due to one of tines 112 or 114 being always engaged and resisting backward translation. With guide wire 30 secured, the user can focus on other areas of the procedure in progress, and then return to advancing or retreating guide wire 30 as needed through the use of guide wire controller 60. At any time, or after guide wire 30 is no longer needed in the given procedure, the user applies a force to release surface 107 or combination surface 108 which causes first or second tines 112 and 114 to disengage with first or second groove array 79a and 79b. With spring tines 112 and 114 disengaged, the user may completely remove translational assembly 80 from stationary assembly 70 and pull guide wire 30 out the body lumen, or the user can unsecure guide wire 30 from translational assembly 80 by loosening lock 84 and pull guide wire 30 through guide wire control device 60. Alternatively, the user can also decouple guide wire control device 60 from deployment device 50 through Luer connector 72 and pull guide wire 30 by means of guide wire control device 60.

Guide wire control device 60 provides substantial guide wire control and improved deployment accuracy of prosthetic valve 42 during a heart valve replacement procedure. Guide wire 30 can be advanced through a lumen of the body and then inserted through guide wire control device 60, or it can be advanced through guide wire control device 60 with lock 84 in the unsecured state. With guide wire in the general desired location within heart 10, translational assembly 80 is engaged to stationary assembly 70 as previously described. With catheter sheath 40 advanced to the general desired location of capsule 44 within heart 10, the user applies a force to actuator 100 to move translational assembly 80 and resulting guide wire 30 to adjust capsule 44 to the precise location, both in depth and radially inside of natural valve 16. This movement may be a forward force to actuator 100 to sequentially engage spring tines 112 and 114 to groove arrays 79a and 79b, or to apply a downward force to actuator 100 to disengage spring tines 112 and 114 and to allow translational assembly 80 and guide wire 30 to move backward. Once prosthetic valve 42 is in the desired precise location, valve 42 is deployed with guide wire control device 60 resisting the "jump" force of valve 42 during deployment. With the successful deployment of valve 42, guide wire 30 can be removed from the body utilizing one of the methods previously described. At any time during the procedure, if guide wire 30 needs to be quickly removed from the body or substantially retracted, the surgeon can quickly apply a downward force to actuator 100 and pull backward guide wire 30. The open back end of stationary assembly 70 provides the means to quickly decouple guide wire 30 from stationary assembly 70.

Alternative Embodiments

Although the preceding descriptions set forth the best mode of the present invention there are numerous alternative embodiments that all fall within the spirit and scope of the present invention.

The best mode of the present invention utilizes alternating grooves arrays which provide translational resolution that exceeds the resolution that grooves can be produced utilizing low cost manufacturing methods, such as injection or die cast molding. With some applications not requiring narrow translational resolution, it may be advantageous to use a single array of grooves. The present invention can utilize a single array of grooves, two arrays that are aligned, or two arrays that are offset. It is possible to use three or more arrays of grooves to achieve very finite resolutions if needed for a particular procedure. The present invention should not be construed to be limited to any particular number of groove arrays or their offsets.

Similar to the alternating groove description above, the present invention utilizes two offset tines for independent motion and engagements with groove arrays 79a and 79b. The best mode is provided to highlight a high level of design flexibility. Offset tines can be used with aligned groove arrays, or spring 110 can have a single tine engaging with a single groove array. For increased translational resolution, spring 110 can have more than two spring tines each engaged with a corresponding groove array. The present invention should not be construed to be limited to any particular number of spring tines or offsets.

Figure 9:
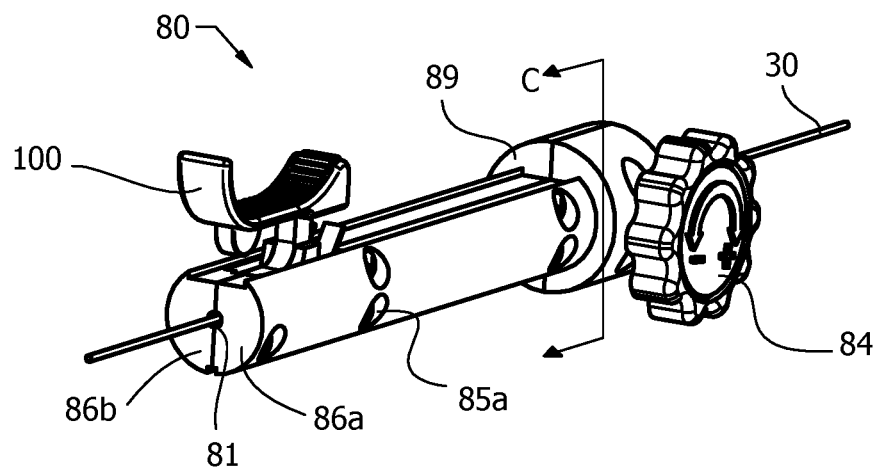
FIG. 9 is a front perspective view of the translating assembly, according to the present invention, and showing section line C.
Figure 16:
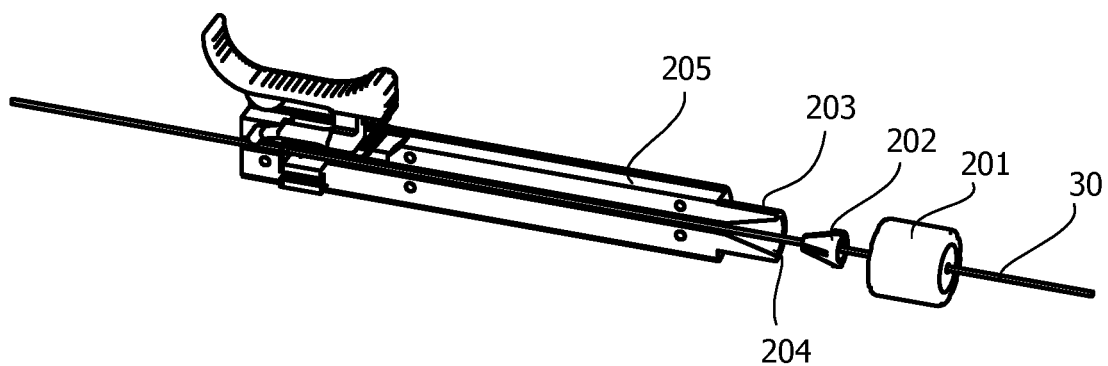
FIG. 16 is a perspective view of translational assembly showing an alternative embodiment guide wire lock mechanism. The translational assembly is shown with the nearest main body hidden to better shown the alternative embodiment lock components.
Figure 17:
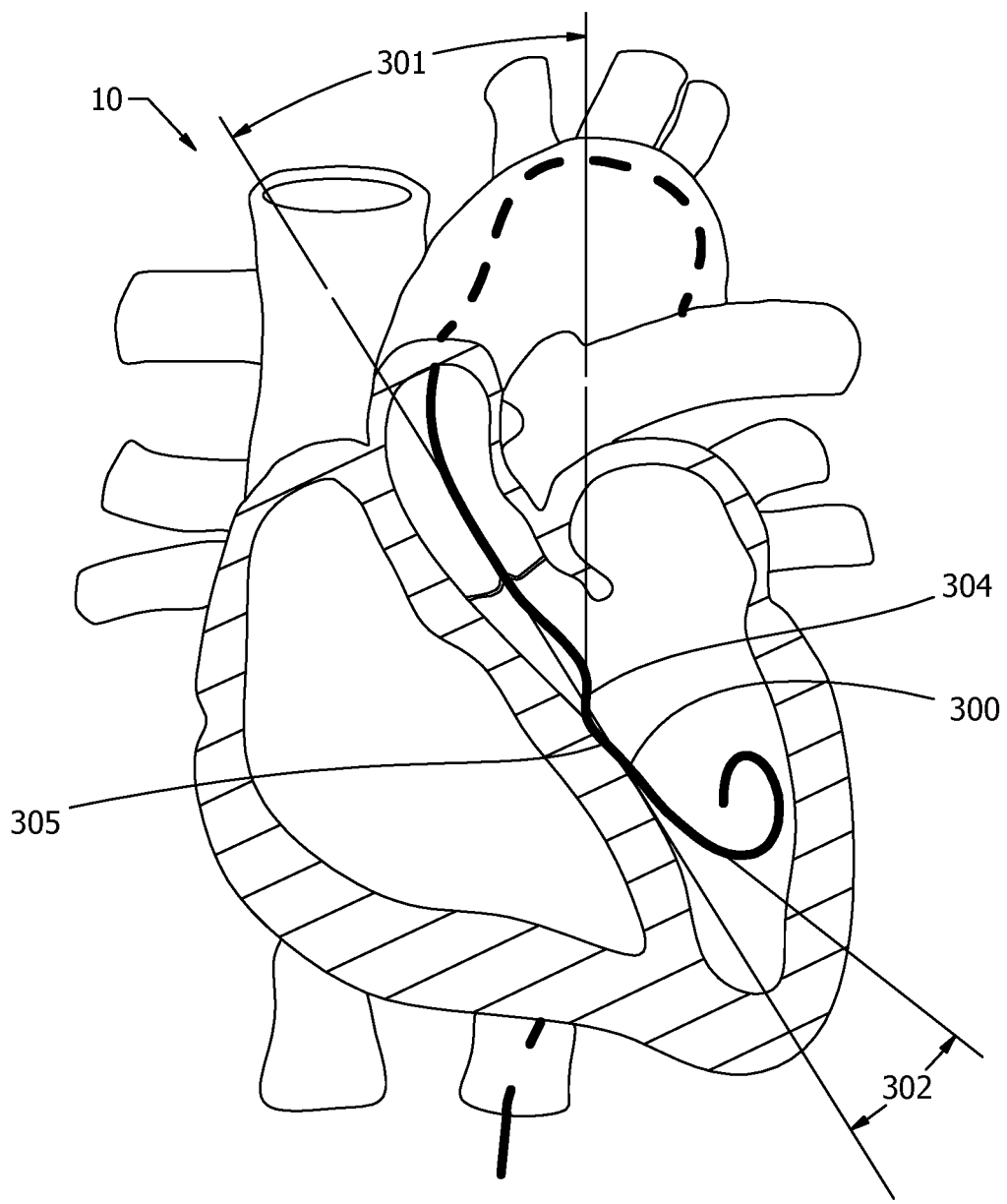
FIG. 17 is a front partial section view of a heart showing the application of an alternative embodiment guide wire end shape for improved alignment of a heart valve.

As shown best in FIG. 9 and FIG. 12, the best mode of the present invention shows lock 84 with screw 83 for applying a radial force to guide wire 30. Screw 83 provides a substantial mechanical advantage and with complaint sleeve 71 they create a large frictional force on guide wire 30. Such a configuration is desirable with guide wire 30 coated with a low friction coating. The best mode of the present invention is capable of creating a 10 to 20 plus pound retention force on a coated guide wire. FIG. 16 shows an example alternative embodiment of lock 84. An alternative sliding member 205 is shown having a conical cavity 204 and an outside thread 203. Conical cavity 204 engages with a collapsing ring 202 that when a turn cap 201 engages with outside thread 203 creates a friction force between collapsing ring 202 and guide wire 30. Turning cap 201 can create a variable frictional force onto guide wire 30 by pushing collapsing ring 202 into conical cavity 204. This alternative embodiment has advantages of greater translation capabilities as cap 201 can be sized to fit within the inside diameter of main body 76. Other embodiments are cable of creating the needed guide wire frictional forces, such as a locking cam, snap ring or adhesive.

To clarify the sprit and scope of the present invention, it should be appreciated that the angle "α" of spring 110 can altered to provide optimal function of a give procedure. Angle "α" is shown greater than ninety degrees to allow it to bend downward out of groove arrays 79a and 79b with a forward force on actuator 100. Alternatively, angle "α" can be made to be less than ninety degrees which would cause spring 110 to resist forward movement of translational assembly 80 but allow reward translation. Furthermore, angle "α" can be approximately ninety degrees which would not allow any sliding movement of translational assembly 80 without actuator 100 causing spring 110 to deflect out of groove arrays 79a and 79b. The best mode for angle "α" is shown at 125 degrees, but any angle falls within the sprit and scope of the present invention providing controlled movement of guide wire 30.

The best mode of the present invention is shown as an add on to existing deployment device 50. It should be appreciated that the advantages of the present invention is not limited to it being an add on device. Rather than utilizing a Luer fitting for connecting two devices, it may be desirable to build the present invention into deployment device 50. A common housing can have a groove array and allow for the controlled movement of translational assembly 80.

FIGS. 17 to 21 show alternative shapes of guide wire 30 which can be used to more optimally center prosthetic valve 42 within heart 10. Guide wire 300 is shown with a complex shape that has bends that can make contact with the walls of heart 10 to better align guide wire 10 and prosthetic valve 42 within annulus 17. An offset section 304 is shown having an angle 301 with respect to annulus 17. Offset section 304 creates a staggered distance for a contact section 305 to make contact with the left interior wall of the patient's heart. Contact section 305 is at an angle 302 with respect to the axis of annulus 17. Combined, a force on the proximal end of guide wire can apply a force between the interior surface of left ventricle 18 and contact section 305 which results in a radial location change of guide wire 30 through natural aortic valve 16. By translating guide wire 30 relative to sheath 40 an optimal location of prosthetic valve 42 can be more easily and quickly achieved over the prior art.

Figure 18:
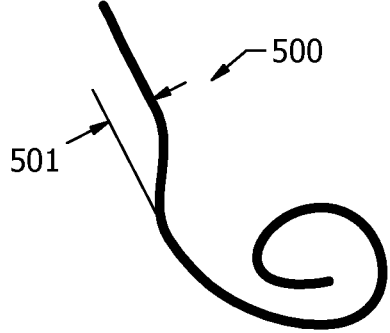
FIG. 18 is an offset guide wire alternative embodiment shape.
Figure 19:
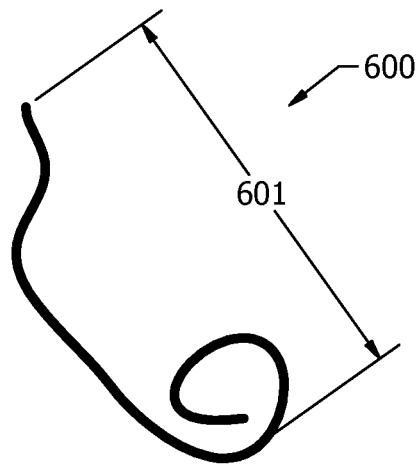
FIG. 19 is a variable length guide wire alternative embodiment shape.
Figure 20:
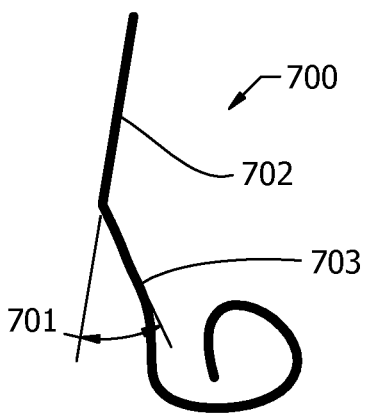
FIG. 20 is a bent guide wire alternative embodiment shape.
Figure 21:
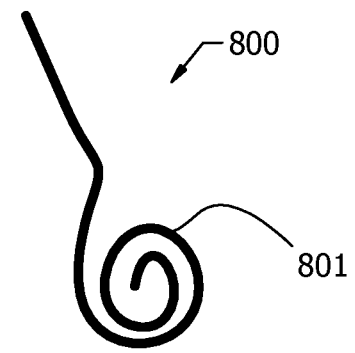
FIG. 21 is a curl guide wire alternative embodiment shape.

FIGS. 18 through 21 show more alternative embodiments of guide wire 30 with any one being optimal for a particular patient's heart. FIG. 18 shows offset guide wire 500 having an offset 501 relative to the main guide wire axis. Offset 501 may be a variable ideally suited for a particular patient's heart. FIG. 19 shows a length guide wire 600 having a distance 601 from the end of the curl to the straight section going through natural valve 16. Length 601 can be optimized for a particular patient's heart and allow guide wire 30 to be pushed against the bottom wall of left ventricle 18 for more optimal location of prosthetic valve 42. FIG. 20 shows a bent guide wire 700 having a straight section 702 and a bent section 703. Bent section 703 is formed at an angle 701 relative to straight section 702. Bent section 703 at angle 701 can be optimized to a particular patient's heart for better alignment of prosthetic valve 42 within annulus 17. FIG. 21 shows a coil guide wire 800 with a coil section 801. The diameter of coil section 801 and the number of turns can be optimized for a particular patient's heart for better alignment of prosthetic valve 42 within annulus 17. Although FIGS. 18 through 21 show individual shape variables, an optimal version of guide wire 30 may be a combination of shapes shown. For instance, an optimal guide wire may be a combination of offset 501, length 601, bend 701 and curl 801. FIGS. 17 to 20 show alternative embodiments of guide wire 30 making them not only suitable for navigating the tortuous pathways of lumens in the body, but optimized to work in the open spaces of the heart.

Figure 22:
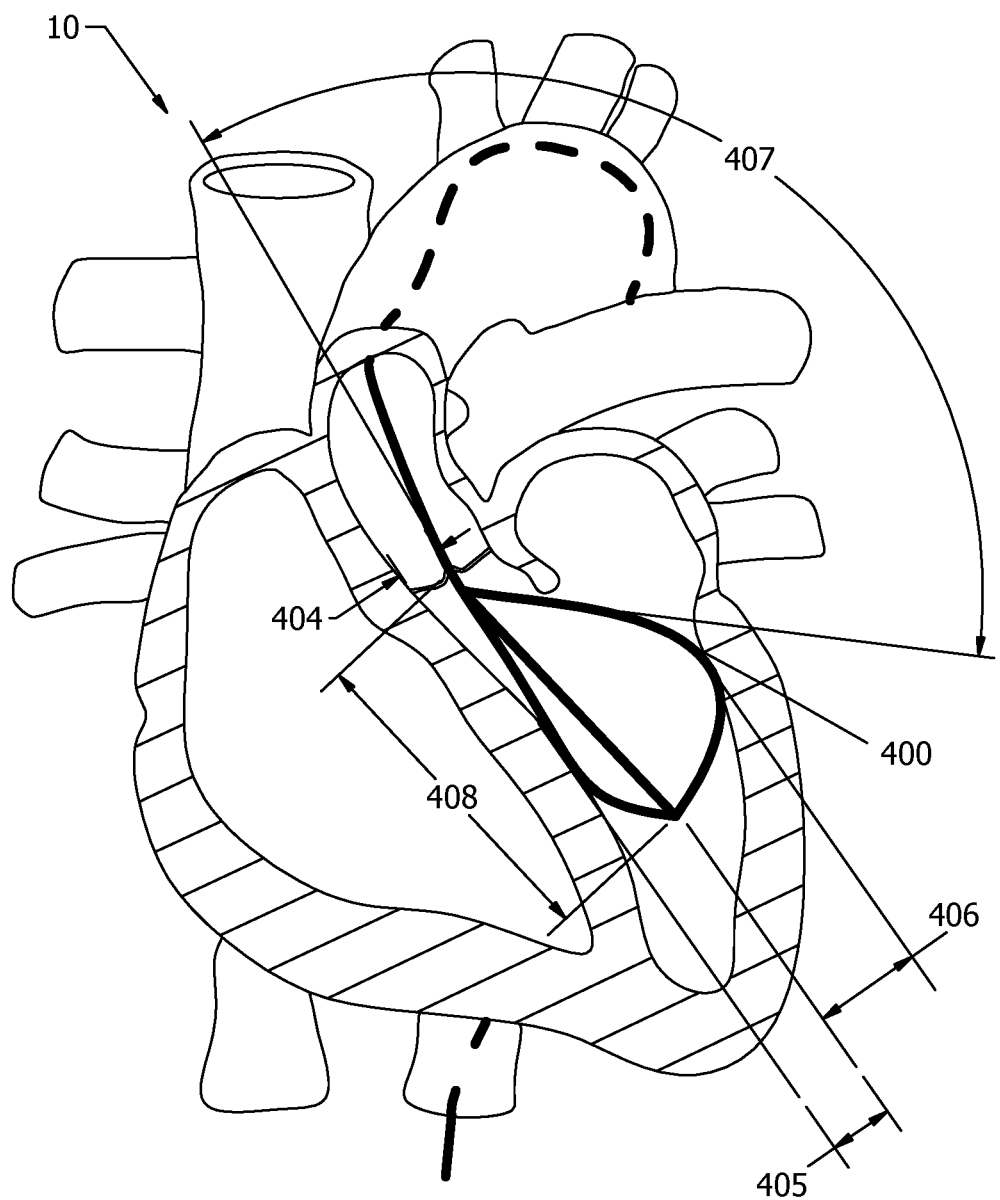
FIG. 22 is a front partial section view of a heart showing the application of an alternative embodiment guide wire having a plurality of strands.
Figure 23:
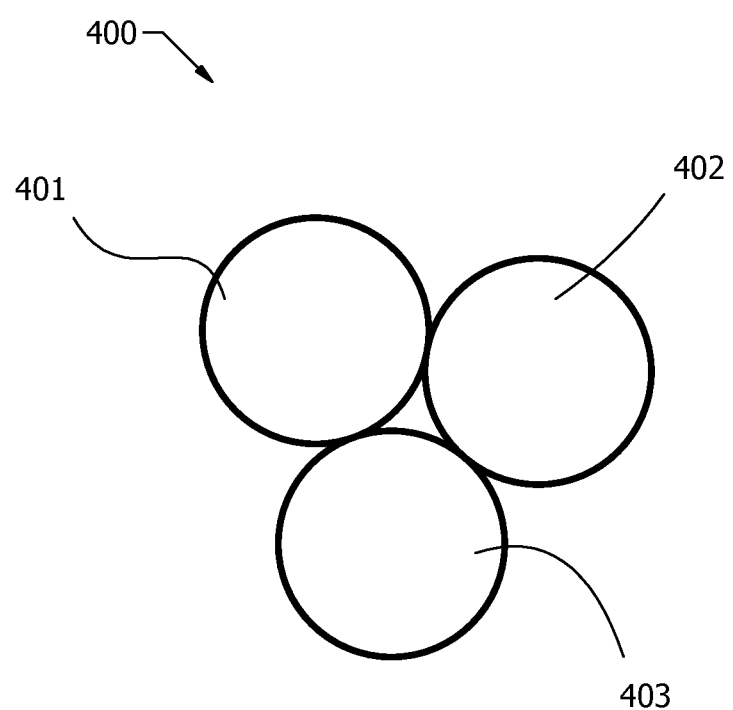
FIG. 23 is a section view of the plurality stranded guide wire of FIG. 22.

FIGS. 22 and 23 show yet another alternative embodiment of guide wire 30 which may be useful for aligning prosthetic valve 42 within heart 10. Guide wire 400, as shown in the collapsed cross section view of FIG. 23, is comprised of first wire 401, second wire 402 and third wire 403. Together the collapsed wires transverse the tortuous pathways and when entering the open space of heart 10 they expand as shown in FIG. 22. Expanded wires 401, 402, and 403 make contact with the walls of heart 10 and provide a structure to apply forces to align prosthetic heart valve 42. It should be appreciated that although three wires are shown, two or more wires can achieve the desired result. Each wire may have a different shape when expanded giving more versatility to align valve 42.

Figure 24:
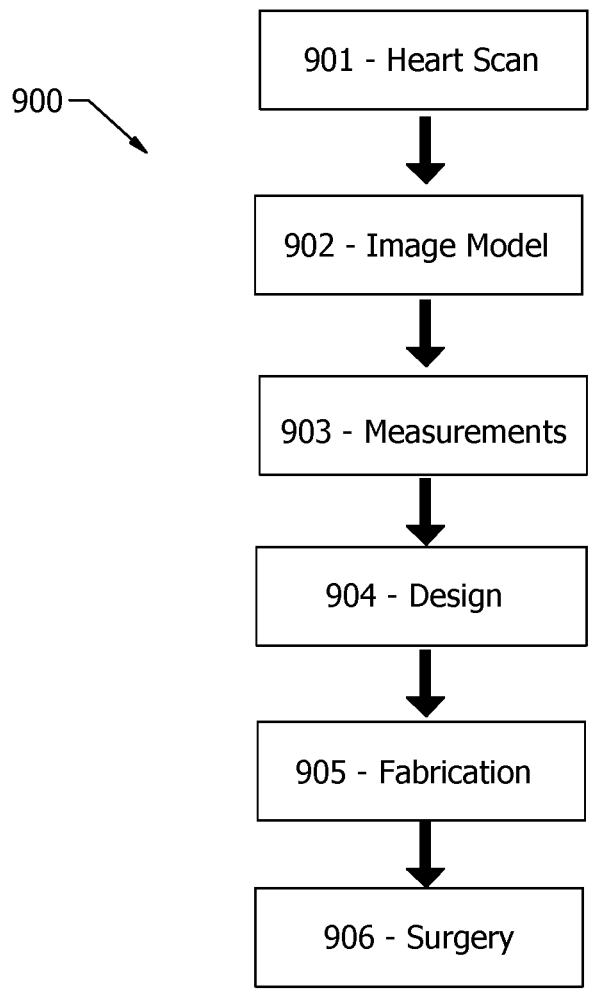
FIG. 24 is a flow diagram for a custom guide wire process.

It should be appreciated that individual patient hearts have different sizes and shapes. Aortic arch 14 may have different bends towards ascending aorta 15 and different diameters. Ascending aorta 15 may transition to annulus 17 at different angles and the length of annulus 17 may vary. The volume of left ventricle 18 can vary as well as its wall locations. As an alternative embodiment, the present invention of optimally locating prosthetic valve 42 can be improved by a custom process 900 which is shown in FIG. 24. Custom process 900 creates a custom guide wire 30 optimized for a particular patient's heart and is comprised of the following steps:

(1) A heart scan 901, such as a CT scan or an MRI, produces either a two dimensional or three dimensional image model 902 of the patient's heart.

(2) A measurement step 903 utilizes image model 902 to find critical attributes of the patient's heart which may include diameters, lengths, profiles and angles.

(3) A design step 904 utilizes the critical attributes of measurement step 903 and applies historical data and algorithms for creating optimized shapes of guide wire 30. Simulations of the optimized shape can be used in conjunction with image model 902 for predicting the performance of optimized guide wire 30. The output of design step 904 may be a two dimensional drawing or a three dimensional computer model of an optimized guide wire 30.

(4) A fabrication step 905 utilizes common guide wire manufacturing methods for producing the output of design step 904. The fabricated of guide wire 30 can be produced at a manufacturing facility and shipped to the surgery center, or the fabricated product can be produced at the hospital utilizing machines capable of producing bends.

(5) Lastly, a surgical step 906 utilizes the optimized guide wire 30 for surgery. As previously described, guide wire 30 is inserted in a lumen of the body and moved to the desired surgical location to repaired or replaced. The optimized version of guide wire 30 more easily navigates the lumens due to its unique shape and stiffness. In the case of heart valve replacement, the optimized version of guide wire 30 makes contact with tissue and the optimal shape and stiffness ideally positions prosthetic valve 42 within the particular patient's heart. The use of guide wire control device 60 in combination with optimized version of guide wire 30 gives the surgeon much control and accuracy over current methods. The goal is to improve the speed and locational accuracy of prosthetic valve 42 while reducing the risk of tissue damage to heart 10.

Other manufacturing embodiments of the present invention are possible and all within the sprit and scope of the present invention. For instance, translating assembly 80 is shown as the best mode of the present invention. The best mode is shown in a way to provide the desired function, but also to allow low cost injection molding manufacturing methods. It should be appreciated that other manufacturing methods can result in a different and optimized construction. For instance, translational assembly 80 may be a single part manufactured with spring 110 within. As another example, actuator 100 may be fabricated as part of sliding member 86*a* and, or, 86*b*. It is possible to 3D print translational assembly 80 in one part that includes the function of spring 110. Spring 110 does not have to be produced from a metallic material to provide the desired function or flexibly engaging with stationary assembly 70, alternatively spring 100 may constructed from a polymeric material. Alternative to the construction described herein, it should be appreciated that the controlled displacement between translational assembly 80 and stationary assembly 70 is accomplished with a spring and a groove which provide the means of variably engaging translational assembly 80 and stationary assembly 70. Rather than utilize a spring on translational assembly 80 and grooves in stationary member 70, stationary assembly 70 may contain a spring and translational assembly 80 may contain grooves. All construction methods fall within the sprit and scope of the present invention.

While the catheter guide wire control device and related methods described herein constitute preferred embodiments of the invention, it is to be understood that the invention is not limited to these precise form of assemblies, and that changes may be made therein without departing from the scope and spirit of the invention as defined in the appended claims.

I claim:

1. A method of utilizing a guide wire for a surgical process which comprises:
    (a) scanning a heart and an annulus of a patient to generate an image;
    (b) measuring said image to determine an optimal position of a prosthetic heart valve relative to the said heart and said annulus;
    (c) forming an internal end of a guide wire to have an optimized shape for aligning said prosthetic heart valve to said optimal position; and,
    (d) utilizing said guide wire with a heart valve deployment device as part of a surgical procedure to deploy said prosthetic heart valve within said patient.

2. The method of claim 1, wherein said utilizing step includes linearly controlling said guide wire with a control device releasably attached to an external end of said guide wire.

3. The method of claim 1, wherein said forming step includes bending an offset shape as part of said optimized shape.

4. The method of claim 1, wherein said forming step includes bending a non-linear shape as part of said optimized shape.

5. The method of claim 1, wherein said forming step includes bending a coil shape as part of said optimized shape.

6. The method of claim 1, wherein said forming step includes bending a plurality of expanding wire strands as part of said optimized shape.

7. A method of utilizing a guide wire for a surgical process which comprises:
    (a) scanning a heart chamber and an artery of a patient to generate an image;
    (b) measuring said image to determine one or more anatomical attributes of said heart chamber and said artery and an optimal position of a prosthetic heart valve;
    (c) forming an internal end of a guide wire to have an optimized shape for locating said prosthetic heart valve within said patient using said one or more anatomical attributes; and,
    (d) utilizing said guide wire within a heart valve deployment device as part of a surgical procedure to deploy said prosthetic heart valve within said patient.

8. The method of claim 7, wherein said utilizing step includes linearly managing said guide wire with a control device connected to said heart valve deployment device and releasably attached to an external end of said guide wire.

9. The method of claim 7, wherein said forming step includes bending an offset as part of said optimized shape.

10. The method of claim 7, wherein said forming step includes bending a non-linear shape as part of said optimized shape.

11. The method of claim 7, wherein said forming step includes bending a coil shape as part of said optimized shape.

12. The method of claim 7, wherein said forming step includes bending a plurality of expanding wire strands as part of said optimized shape.

13. The method of claim 7, wherein said utilizing step includes making said guide wire make contact with a wall of said heart causing an axis of said prosthetic heart valve to align to an axis of said artery.

14. A method of utilizing a guide wire for a surgical process which comprises:

(a) scanning a heart and a connected lumen of a patient to generate an image;
(b) measuring said image to determine one or more anatomical attributes of said heart and said lumen, and an optimal position of a prosthetic heart valve relative to said heart and said lumen;
(c) forming an internal end of a guide wire to an optimized shape for locating said prosthetic heart valve to said optimal position using said one or more anatomical attributes;
(d) utilizing said guide wire as part of a surgical procedure within said patient wherein said internal end of said guide wire makes contact with a wall of said heart and aligns said prosthetic heart valve with an axis of said lumen; and,
(e) deploying said prosthetic heart valve by moving an actuator of a deployment device.

15. The method of claim 14, wherein said utilizing step includes translating said guide wire with a linear control device connected to said heart valve deployment device and releasably attached to an external end of said guide wire.

16. The method of claim 14, wherein said forming step includes bending an offset as part of said optimized shape.

17. The method of claim 14, wherein said forming step includes bending a non-linear shape as part of said optimized shape.

18. The method of claim 14, wherein said forming step includes bending a coil shape as part of said optimized shape.

19. The method of claim 14, wherein said forming step includes combining a plurality of expanding wire strands to create said guide wire.

* * * * *